United States Patent [19]

Kimura

[11] Patent Number: 4,846,155

[45] Date of Patent: Jul. 11, 1989

[54] VIDEO ENDOSCOPE APPARATUS WITH AUTOMATIC FOCUSING CONTROL

[75] Inventor: Kenji Kimura, Tachikawa, Japan

[73] Assignee: Olympus Optical Co. Ltd., Tokyo, Japan

[21] Appl. No.: 247,851

[22] Filed: Sep. 22, 1988

[30] Foreign Application Priority Data

Sep. 30, 1987 [JP] Japan ................. 62-247287

[51] Int. Cl.$^4$ .............................. A61B 1/04
[52] U.S. Cl. ......................... 128/6; 358/98
[58] Field of Search .................. 128/4, 6; 358/98

[56] References Cited

U.S. PATENT DOCUMENTS

| 4,600,938 | 7/1986 | Sluyter et al. | 358/98 |
| 4,600,939 | 7/1986 | Sluyter et al. | 358/98 |
| 4,618,884 | 10/1986 | Nagasaki | 358/98 |
| 4,621,618 | 11/1986 | Omagari | 128/6 |

FOREIGN PATENT DOCUMENTS 53-12193 2/1978 Japan .

Primary Examiner—William H. Grieb

Attorney, Agent, or Firm—Stevens, Davis, Miller & Mosher

[57] ABSTRACT

In a video endoscope apparatus in which an objective and a solid state imaging sensor are provided in the distal end portion of the inserting portion thereof, which is to be inserted into a cavity of a body, and the image of the wall of the cavity picked-up by the solid state image sensor is displayed on a monitor, the solid state image sensor is vibrated at a predetermined frequency of 10 Hz in the direction of the optical axis of the objective by means of the piezoelectric element, the peak value of the image signal supplied from the solid state image sensor is detected on each horizontal scanning line, the peak value detected thereby is passed through a band pass filter having a central frequency of 10 Hz, the signal passed through the band pass filter is synchronously detected by using a sampling signal which has a frequency of 10 Hz and is synchronized with said vibration, a focusing error correcting signal is generated by comparing a synchronously detected signal and a reference signal, and the solid state image sensor is moved in and in-focused position by supplying the focusing error correcting signal to the piezoelectric element.

9 Claims, 8 Drawing Sheets

FIG_2
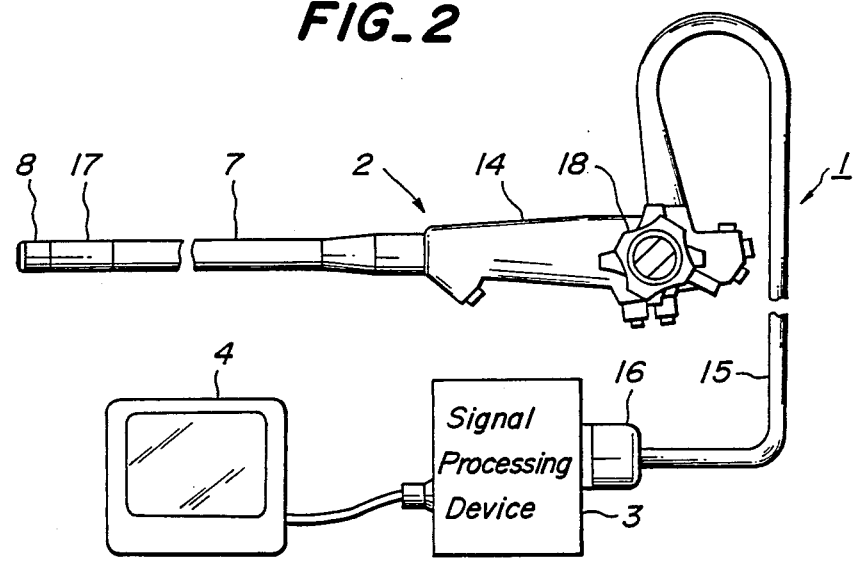
FIG_3A    FIG_3B
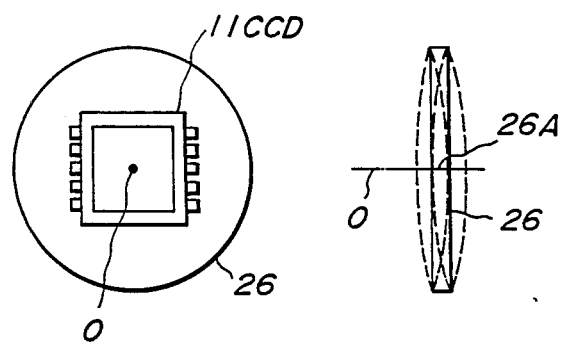

FIG_5
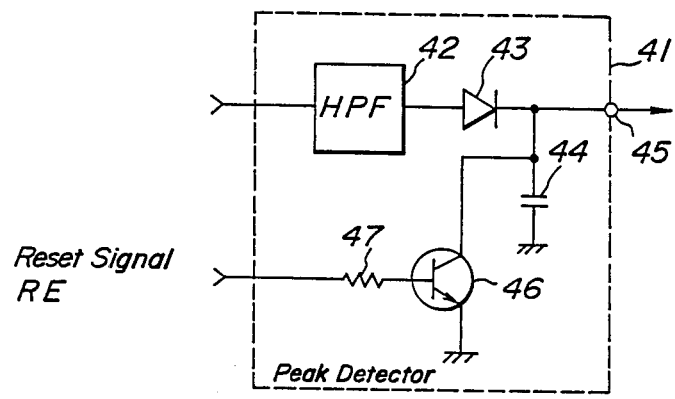
FIG_6A Output of HPF 42
FIG_6B Reset Signal RE
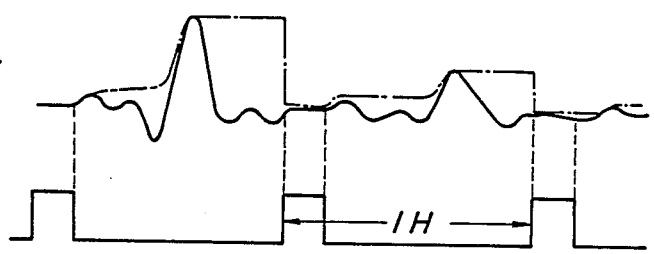
FIG_7
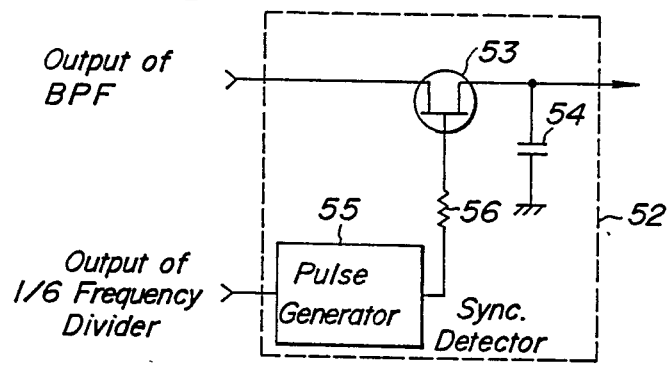

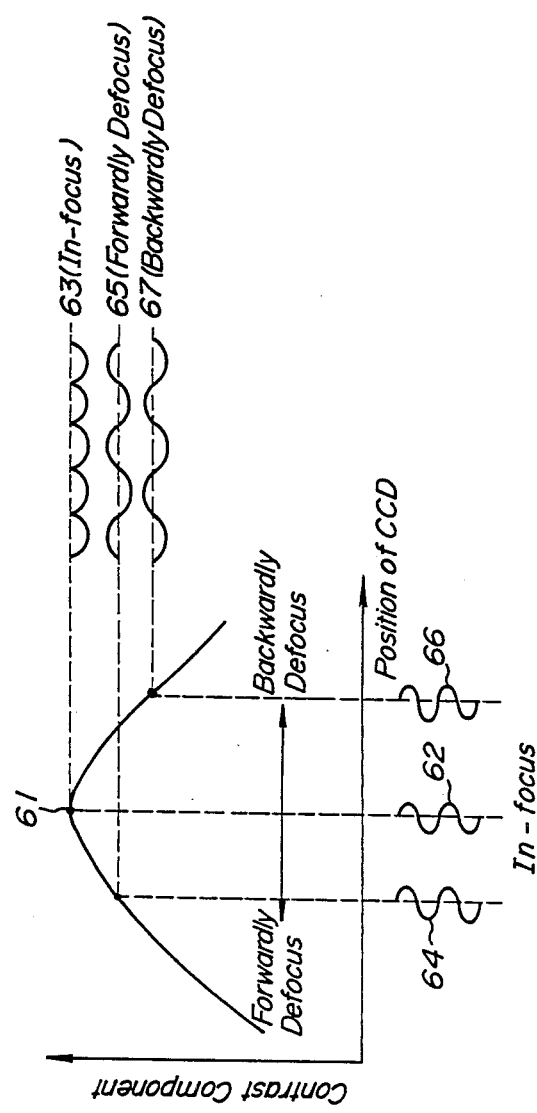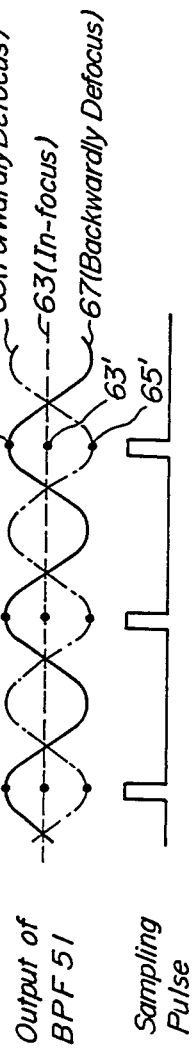

FIG_10
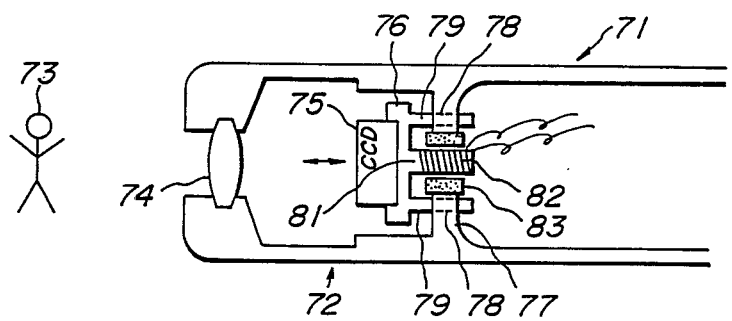
FIG_11
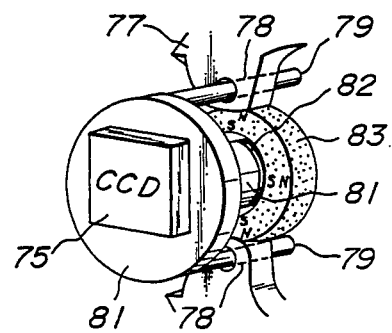
FIG_12
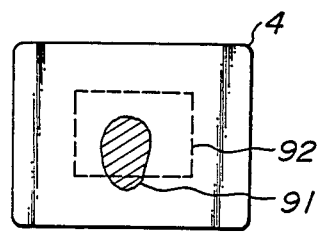

FIG_13
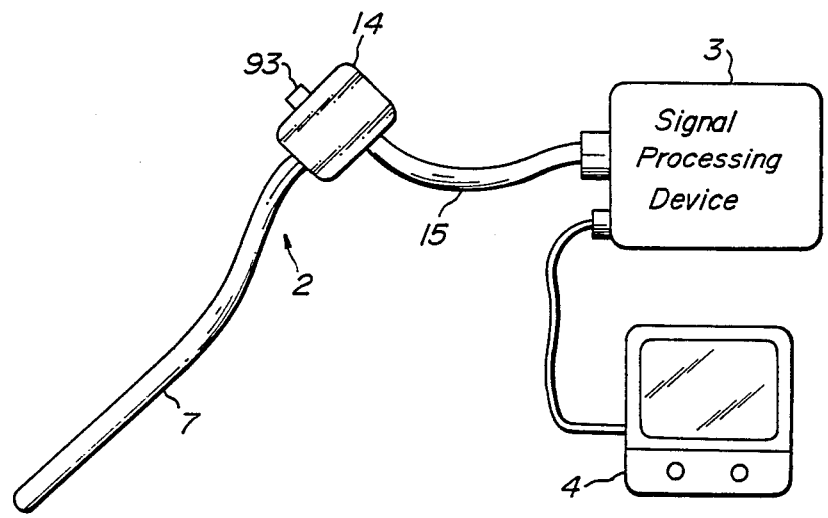
FIG_14
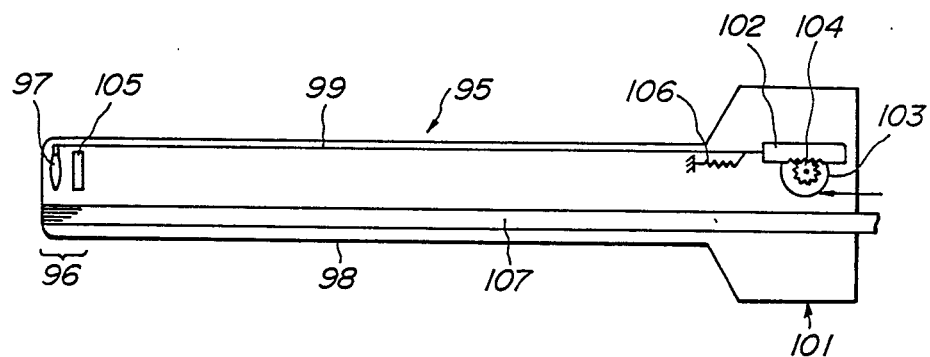

FIG_15
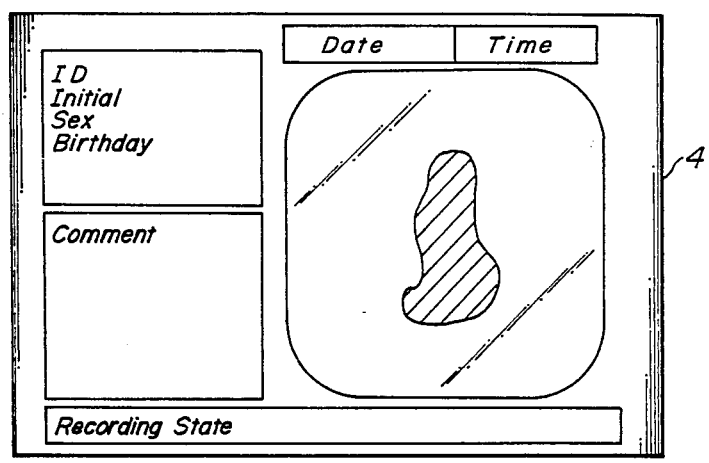

VIDEO ENDOSCOPE APPARATUS WITH AUTOMATIC FOCUSING CONTROL

BACKGROUND OF THE INVENTION

Field of the Invention and Related Art Statement

The present invention relates to a video endoscope apparatus with an automatic focusing control having a function that an object is imaged in the best focused condition automatically without manual adjustment.

Heretofore, an electronic endoscope having an image sensor arranged in a distal end thereof has been developed and utilized. Such an electronic endoscope is called a video endoscope. In the video endoscope, the image sensor is formed by a solid state image sensor such as charge-coupled device and a static induction transistor device. The video endoscope has an advantage that images can be more easily recorded and reproduced in comparison with optical endoscopes.

As is well known in the art, when observing a scope image picked up by the video-endoscope, the observation distance is changed over a very wide range from several millimeters to several ten centimeters. It is because of the fact that when a morbid portion of a cavity of a living body is observed in comparison with a surrounding portion, the distal end of the scope is separated from the morbid portion by several tens centimeters, while when the morbid portion is observed in detail by an enlarged image, it is necessary to place the distal end of video endoscope closer to the morbid portion.

Under such situation, it is extremely difficult to form always focused images of the object on the imaging surface of the CCD for the wide range of the observation distance by the video endoscope using a fixed-focus optical system. From the viewpoint of diagnosis, it is desired to image the object always in the in-focused condition over the wide range of the observation distance.

In Japanese Patent Publication Kokai Sho No. 53-12,193, there is disclosed an endoscope in which a focusing adjustment is conducted by moving an objective provided in the distal end. However, there is a disadvantage that the constitution of the light source device thereof is complex because there must be provided a light source for the focus detection separately from the light source for illuminating the object.

SUMMARY OF THE INVENTION

The present invention has for its object to provide a video endoscope apparatus with an automatic focus control, in which the in-focused condition is automatically established over the wide range of the observing distance, so that a sharp scope image can be always obtained.

According to the present invention, the video endoscope apparatus with an automatic focus control comprises a video endoscope including an insertion section to be insertable into an object under inspection and having a distal end and a proximal end, an objective lens system arranged within the distal end of the insertion section and forming an optical image of the object, and an image sensor arranged within the distal end of the insertion section and receiving the optical image of the object to produce an image signal;

a signal processing unit connectable to said video endoscope and processing the image signal produced from said image sensor to derive a processed image signal;

a monitor having a screen for displaying the processed image signal; and an automatic focus controlling means including an oscillator for producing a vibration signal having a constant frequency, a vibrating means for vibrating said objective lens system and image sensor relative to each other in a direction of an optical axis of the objective lens system in accordance with the vibration signal supplied from the oscillator, a focus detecting means for detecting a focus condition of the optical image formed on the image sensor by the objective lens system by processing the image signal supplied from said image sensor, and a focus error correcting means for deriving a focus error correcting signal from the focus condition detected by said focus detecting means and moving said objective lens system and image sensor relative to each other in the direction of the optical axis of the objective lens system in accordance with said focus error correcting signal so as to attain the in-focused condition.

BRIEF DESCRIPTION OF THE DRAWINGS

FIG. 2 is a schematic view illustrating the external appearance of the video endoscope apparatus shown in FIG. 1;

FIGS. 3A and 3B are schematic views showing the piezoelectric element to which the CCD is secured;

FIG. 5 is a circuit diagram illustrating the peak detector;

FIG. 6 is a schematic view showing the wave shapes for explaining the operation of said peak detector illustrated in FIG. 5;

FIG. 7 is a circuit diagram of the synchronous detector;

FIG. 8 is a graph for explaining the function of the auto focus servo circuit;

FIGS. 9A and 9B are schematic views showing the wave shapes for explaining the function of the synchronous detector;

FIG. 10 is a schematic view showing the structure of the imaging portion of a second embodiment of the video endoscope apparatus according to the invention;

FIG. 11 is a perspective view representing the vibrating portion of the video endoscope shown in FIG. 10;

FIG. 12 is a schematic view showing the monitor surface on which the marker and the image of object, i.e. morbid portion are displayed;

FIG. 13 is a schematic view illustrating the operating portion of the video endoscope on which the on-off switch is provided;

FIG. 14 is a schematic view representing the principal portion of a third embodiment of the video endoscope apparatus according to the invention; and FIG. 15 is a schematic view showing another embodiment of the display on the monitor.

DESCRIPTION OF THE PREFERRED EMBODIMENTS

FIGS. 1 to 9 show a first embodiment of the video endoscope apparatus according to the invention. As shown in FIG. 2, the video endoscope apparatus 1 comprises a video endoscope 2, a signal processing device 3 in which a signal processing system and a light source system are provided, and a color monitor 4 for displaying color images of an object in accordance with the image signals supplied from said signal processing device 3.

Figure 1:
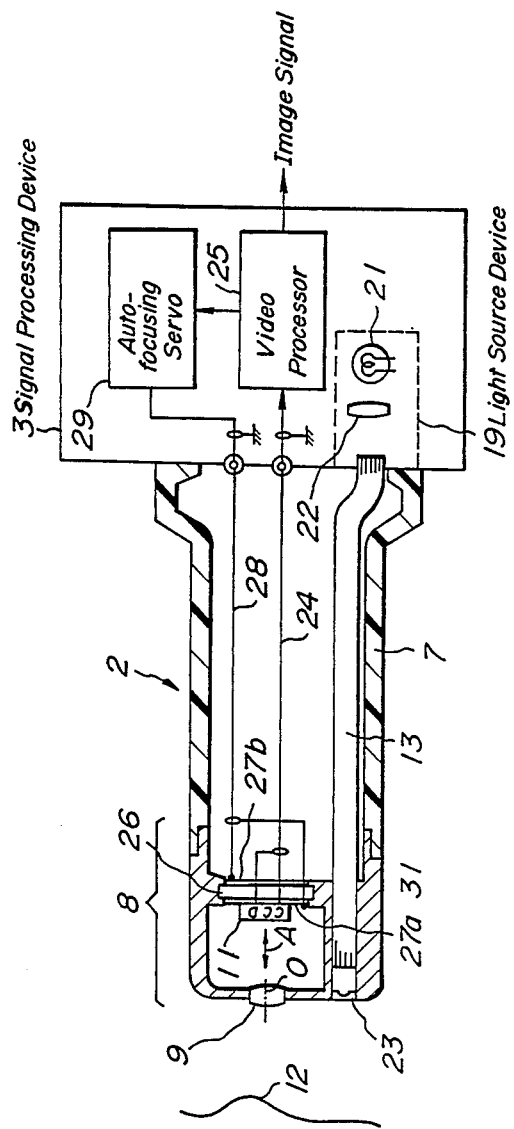
FIG. 1 is a schematic view showing the principal construction of a first embodiment of the video endoscope apparatus according to the invention.

Said video endoscope 2 comprises a thin and long inserting portion 7 which is formed to be flexible for the purpose of inserting itself into a cavity of a body. And, as shown in FIG. 1, there is provided an objective 9 in a distal end 8 of the inserting portion 7 to form an optical image of an object 12. On the focal plane of this objective 9, there is arranged a charge-coupled device (CCD) 11 which receives the optical image of the object 12 and supplies an electric image signal.

Further, in the inserting portion 7, a light guide 13 is inserted therethrough to transmit illuminating light. The light guide 13 is further extended through an operating portion 14 and a universal code 15 and is detachably connected to the signal processing device 2 with the aid of a connector 16. Then the illuminating light is made incident upon an incident end surface of the light guide 13. At the same time, the CCD 11 is electrically connected to the signal processing system via the universal code 15 and connector 16. As illustrated in FIG. 2, a bending portion 17 is formed adjacent to the distal end portion 8, and this bending portion can be bent by rotating a knob 18 provided on the operating portion 14.

As shown in FIG. 1, in the signal processing device 3, there is provided a light source device 19 including a light source lamp 21 for emitting white light and a condenser lens 22 for introducing the white light emitted from the lamp onto the incident end surface of the light guide 13. The illuminating light transmitted through the light guide 13 exits from an exiting end thereof and is projected upon the object 12 by means of an illumination lens 23. Then, light reflected from the object 12 is collected by the objective 9 to form the optical image of the object on the CCD 11, and the image signal generated from the CCD is supplied to a video processor 25 via a signal cable 24. In the video processor 25, to the image signal are added horizontal and vertical synchronizing signals to derive a television image signal.

Figure 4:
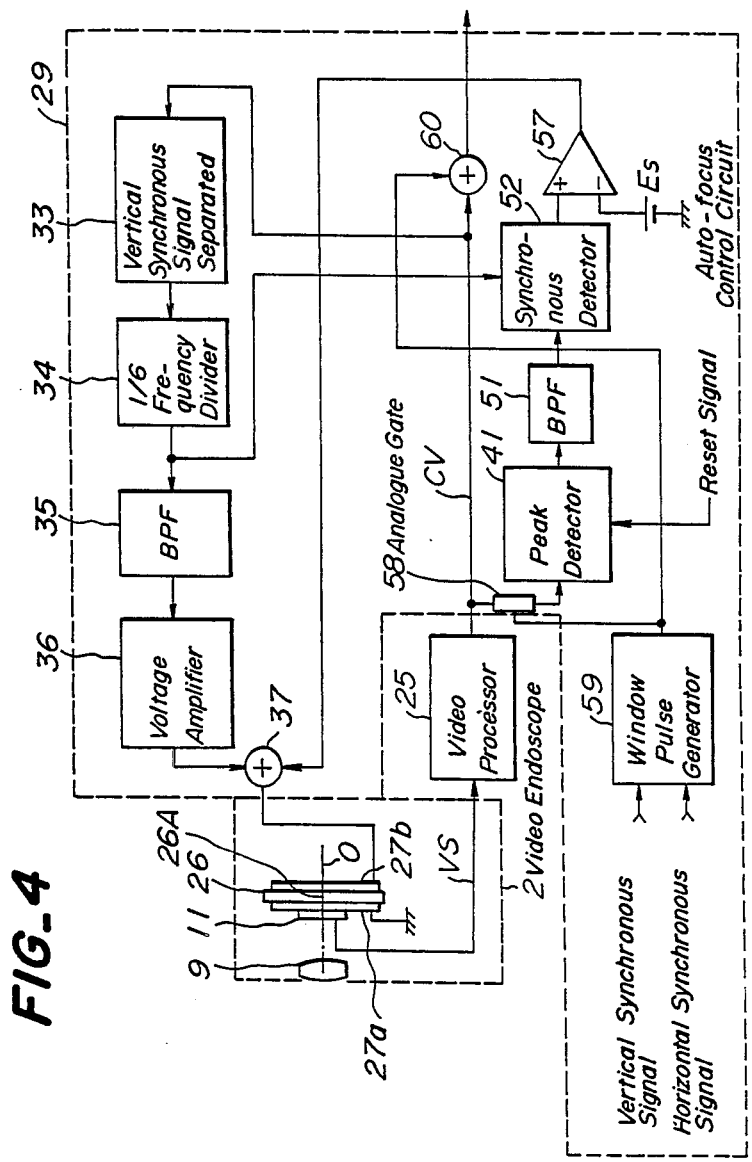
FIG. 4 is a block diagram showing the structure of the auto focusing servo circuit.

In the present embodiment, the CCD 11 is fixed on a plate-shaped piezoelectric element 26 by means of adhesion as illustrated in FIGS. 1, 3 and 4. The piezoelectric element 26 is used as an electromechanical transducing element.

When a voltage is applied across electrodes provided on opposite surfaces of the piezoelectric element, the electric energy is converted into the mechanical energy, and thus mechanical strain is generated in the piezoelectric element. In this first embodiment, an alternating voltage is applied to electrodes 27a and 27b, which are provided on opposite surfaces of the piezoelectric element 26, to vibrate the piezoelectric element 26 in a direction shown by an arrow A in FIG. 1, i.e. in the direction of the optical axis of the objective 9.

An electric cable 28 is connected to the electrodes 27a and 27b, and the driving voltage generated from an auto focusing servo circuit 29 in the signal processing device 3 is applied to the cable 28.

In this first embodiment, the piezoelectric element 26 has a circular shape as shown in FIG. 3A, and the square shaped CCD 11 is fixed on the piezoelectric element 26, for example, by an adhesive agent such that the centers of the piezoelectric element 26 and the CCD 11 are coincident with each other. For instance, the alternating voltage having a frequency of 10 Hz and an amplitude of about 50 Vpp is applied to the both electrodes on the piezoelectric element 26 as the vibrating voltage, and the piezoelectric element 26 is vibrated at a frequency of 10 Hz in the direction of the optical axis of the objective 9 as shown in FIG. 3B.

As illustrated in FIG. 1, a ring-shaped slit 31 is formed in the cylindrical housing of the distal end portion 8 of the scope and the circumference of the piezoelectric element 26 is clamped in the slit.

As shown in FIG. 3B, the center portion of the piezoelectric element 26 is vibrated with the largest amplitude by the application of the vibration voltage. Also, in this piezoelectric element 26, the moving amount on a concentric circle thereof is always same. Therefore, when the CCD 11 is fixed to the center of the piezoelectric element 26, the CCD is vibrated, while a plane of the CCD is kept always perpendicular to the optical axis.

FIG. 4 shows the automatical focusing servo circuit 29 for vibrating the CCD 11 at the constant frequency and for moving the CCD toward an in-focused position.

The color image signal VS of the CCD 11 is supplied to the video processor 25 in the signal processing device 3, and is converted thereby into a color television signal CV of, for example, NTSC system. This color television signal CV is supplied to a vertical synchronizing signal separating circuit 33, and a vertical synchronizing signal having a frequency of 60 Hz is extracted. This extracted vertical synchronizing signal is supplied to a frequency divider 34, in which the frequency of the output signal is divided by six. In this manner, the vertical synchronizing signal is transformed to a square wave signal having a frequency of 10 Hz. The output of the frequency divider 34 is supplied to a band pass filter 35 (hereinafter, mentioned as BPF) having a central frequency of 10 Hz. Then, the square wave is transformed to a sine wave of the frequency of 10 Hz.

The output of said BPF is amplified by a voltage amplifier 36 to derive the sine wave vibration signal having the amplitude of 50 Vpp. And then, the amplified vibration voltage is applied to the electrode 27b arranged on the piezoelectric element 26 via a mixing device 37. Since the other electrode 27a is connected to the ground voltage, when the sine wave voltage having the amplitude of 50 Vpp is applied, the voltage at the electrode 27b changes in accordance with the sine wave having amplitudes of ±25 V. As a result, the piezoelectric element 26 vibrates at the frequency of 10 Hz, and at the center point 26A of the circular-shaped piezoelectric element 26, the vibrating amount becomes maximum. In this first embodiment, said vibrating amount of the center portion 26A of the piezoelectric element is about ±100 μm viewed in the optical axis direction.

The color television signal CV from the video processor 25 is also supplied to a peak detector 41 via an analog gate 58, which will be explained later, to extract a peak value of the color television signal for every one horizontal scanning period (1 H). Usually the peak value of the image signal corresponds to the highest contract, and when the image becomes defocused, the peak value of the image signal becomes smaller.

FIG. 5 is a circuit diagram showing the detailed structure of the peak detector 41. The color television signal CV supplied from the video processor 25 is provided to a high pass filter 42 to extract the high frequency component of the color television signal CV. An envelope of the output of the high pass filter (hereinafter, mentioned as HPF) is then detected by a diode 43, and the detected output is charged in a capacitor 44. Therefore, the peak value of the image signal is derived at an output terminal 45. This peak value varies in accordance with contour, contrast, etc. of the object for every one horizontal scanning period.

To this end, the electric charge stored in the capacitor 44 is resetted by a switching transistor 46. That is to say, a reset signal RE is applied to a base of the transistor 46 via a resistor 47. When the reset signal is applied to the base, the collector-emitter path of the transistor is switched on, so that the electric charge in the capacitor 44 is discharged therethrough.

Since the pulse width of said reset signal RE is corresponding to the horizontal blanking width of the color television signal CV, the horizontal synchronous pulse can be used for the resetting pulse. Thus, the output signal of the peak detector 41 is renewed for every horizontal scanning period.

FIGS. 6A and 6B are wave shapes showing the operation of the peak detector 41.

The output of HPF 42 shown in FIG. 6A is detected by the diode 43 and the peak value of the detected output is charged in the capacitor 44 until the capacitor is discharged by the reset signal RE shown in FIG. 6B. In this manner, peak values within portions of respective scanning lines which are extracted by a window produced by the analog gate 58 are derived as shown by a dash and dotted line in FIG. 6A. At the end of every horizontal scanning period, the resetting is conducted in accordance with the reset signal RE which is synchronized with the horizontal blanking period of the color television signal, as shown in FIG. 6B.

As shown in FIG. 4, the output of the peak detector 41 is supplied to a band pass filter 51 having a central frequency of 10 Hz which is the same as the vibrating frequency of the piezoelectric element 26. An output signal from the band pass filter 51 has a shape of the sine wave and is further supplied to a synchronous detector 52 to which the output signal of the frequency divider 34 is applied as a detecting signal. Therefore, the modulating component having the frequency of 10 Hz due to the vibration of the piezoelectric element 26 is synchronized with the detecting signal.

The detailed structure of the synchronous detector 52 is shown in FIG. 7. In this embodiment, the synchronous detector 52 is of the sample and hold type.

The output of the BPF 51 is supplied to a source of a field effect transistor FET 53 serving as an analogue switch, the drain thereof being connected to the output of the synchronous detector 52 as well as to the ground via a capacitor 54, which is used for holding the output of the sample and hold circuit. The synchronous detecting signal from the detector 52 is supplied to a pulse generator 55 for generating a sampling pulse. The sampling pulse generated from the pulse generator 55 is applied to the gate of the FET 53 via a resistor 56. This pulse generator 55 generates the sampling pulse synchronized with the input signal to the frequency divider 34. The signal sampled by the sampling pulse is kept in the capacitor 54 and is applied to one input of a differential amplifier 57. To the other input of the differential amplifier 57, is applied a reference voltage Es, and thus the difference between the signals applied to both inputs is amplified and outputted from the output of the amplifier 57. The output of said differential amplifier 57 is supplied to the mixing device 37.

The analogue gate 58 is controlled by a window pulse generator 59 which is triggered in accordance with a vertical synchronous signal VD and a horizontal synchronous signal HD and generates a window pulse.

Said window pulse serves to extract a portion of the image which is selectively used to detect the focus condition. Generally, the center portion of the image is selected by the window, and then the window pulse generator 59 supplies the window pulse such that a portion of the image signal which situates within the window is selectively supplied to the peak detector 41, and therefore the focus condition of a part of the image within the window is detected. In the present embodiment, the window pulse is supplied to mixing device 60 and is added to the color television signal CV. Therefore, the window area in which the automatic focus control is conducted is displayed on the monitor screen in the real time.

The automatic focus control system of the first embodiment is structured in the above mentioned manner, and now the operation thereof will be explained in the following.

In the band pass filter 51 having the central frequency of 10 Hz shown in FIG. 4, there is no output signal when the CCD 11 is in the in-focused position, but a sine wave having the frequency of 10 Hz and synchronized with the vibration of the piezoelectric element 26, is generated when the CCD is in defocused positions. The sign or phase of this sine wave of 10 Hz is inverted in accordance with the position of the CCD 11 with respect to the focal plane of the objective 9.

FIG. 8 is a graph showing the relationship between the output of the peak detector 41 and the position of CCD 11. When the CCD 11 is just in the in-focused position, the contrast component shows the maximum value, as shown by a reference numeral 61. Thus, when the CCD 11 is vibrated at the in-focused position as illustrated by a wave indicated by a reference numeral 62, the half-wave rectified signal has the frequency of 20 Hz as indicated by a reference numeral 63. On the other hand, when the CCD 11 is vibrated at a forwardly de-focused position which situates closer to the objective with respect to the focal plane as shown by a wave 64, the half-wave rectified signal has the frequency of 10 Hz as illustrated by a wave 65. Similarly, when the CCD 11 is vibrated at a backwardly defocused position which situates far from the objective with respect to the focal plane as illustrated by a wave 66, the half-wave rectified signal has the frequency of 10 Hz as indicated by a wave 67. In this case, the signals of 10 Hz have opposite signs, i.e. the phases of these signals are deviated by 180° from each other.

FIG. 9A shows the half-wave rectified signals 63, 65 and 67 at the in-focused and de-focused positions, and FIG. 9B illustrates the sampling pulse. When the FET 53 of the synchronous detector 52 is switched on in the rhythm of sampling pulse, electric potentials indicated by reference numerals 63', 65' and 67' are sampled and held in the capacitor 54 in accordance with the focusing state of the CCD 11. The reference numerals 63, 65 and 67 represent the output signals of BPF 51 which is illustrated in FIGS. 4 and 8. The reference numeral 63 shows the signal when the CCD 11 is in the in-focused position, and then the primary component of the modulated component is 20 Hz. Since the center frequency of the BPF 51 is 10 Hz, the modulated signal having the frequency of 20 Hz is not outputted from the BPF 51 as shown by the reference numeral 63 in FIG. 9A.

On the other hand, when the CCD 11 is in the de-focused position, the modulated component having the frequency of 10 Hz is generated and becomes larger in accordance with the degree of defocusing, as shown by the reference numerals 65 and 67 in FIG. 9A. The reference numeral 65 shows that the CCD 11 is in the forwardly de-focused position, and contrary, the reference numeral 67 shows that the CCD 11 is in the backwardly de-focused position. The phases of the defocused signals are deviated by 180° from each other.

Since the sampling pulse is coincided with the peak point of the half-wave rectified signal, the output signal of the synchronous detector 52 is the direct voltage whose amplitude changes in accordance with the amount and the direction of the defocus with respect to a voltage $E_F$ which is generated in the in-focused condition. The output voltage of the synchronous detector 52 is applied to the differential amplifier 57, and is compared with the reference voltage $E_s$ therein. The difference between the output voltage and reference voltage $E_s$ represents the focus error correction signal which is mixed with the vibrating signal for driving the piezoelectric element 26 in the mixing device 37. The mixed vibration and correction voltages are applied to the piezoelectric element 26. Said reference voltage $E_s$ for the differential amplifier 57 is set to the voltage $E_F$ corresponding to the voltage when the CCD 11 is in the in-focused position.

The automatic focus control circuit 29 has such a negative feedback that the CCD 11 is automatically moved into the in-focused position. That is to say, as shown in FIGS. 9A and 9B, the defocus signals 65 and 67 have the opposite signs, and in case that these signals are synchronously detected by the sampling pulse having the center frequency of 10 Hz, these signals per se are transformed to the sine wave, but the polarities of the synchronously detected signals are opposite to each other. As shown in FIGS. 9A and 9B, when the CCD is defocused forwardly, the focus error correction signal has a negative polarity, and when the CCD is defocused backwardly, the signal has the positive polarity. Therefore, in case that the CCD 11 is defocused forwardly, the piezoelectric element 11 is shifted backward until the CCD becomes in the in-focused position. In case that the CCD 11 is defocused backwardly, the servo system also works to move the CCD 11 forwardly into the in-focused position. Of course, when the CCD 11 is just in the in-focused position, the servo system works to keep this in-focused state. Therefore, even in case the distance between the object and the objective is changed, the sharp image of the object can be always obtained without adjusting the focus manually.

FIG. 10 is a schematic view showing the construction of a second embodiment of the system for driving the CCD, and FIG. 11 is a perspective view showing a major part of said system. In the first embodiment, the CCD 11 is vibrated by the piezoelectric element 26. But in this second embodiment, a distal end portion 72 of a video endoscope 71 is formed in a cylindrical body and comprises an objective 74 arranged on the front end thereof, and a CCD 75 secured to a movable member 76 in the vicinity of a focal plane of the objective forming an optical image of an object 73. A concave portion is formed in the front end surface of the movable member 76 and the CCD 75 is fixed into the concave portion by adhesive agent. On the rear end surface of this movable member 76, slidable shafts 79, 79 and a yoke 81 are provided, the shafts being passed through holes 78, 78 which are formed in a ring-shaped wall 77, and the yoke being provided at the center position of the rear surface of the movable member. A coil 82 is wound around the yoke 81, and the assembly of the yoke 81 and coil 82 is passed through a center hole of a ring-shaped permanent magnet 83 which is secured to the inner wall of the ring-shaped wall 77. The ring-shaped magnet 83 is polarized in the radial direction as shown in FIG. 11. In this manner, the driving system using the moving coil is composed. Then, the force for moving the movable member 76 into the direction of the optical axis of the objective 74 is generated in accordance with the direction of the electric current supplied to the coil 82.

Thus, in the second embodiment, the automatic focus control is realized by supplying the composite signal of the vibration signal and the focus error correction signal to the moving coil 82. In this embodiment, a current amplifier is used instead of the voltage amplifier. It should be noted that in FIG. 10, the light guide is omitted for the sake of simplicity.

FIG. 12 is a schematic view showing the monitor screen on which the image of the object is displayed. A morbid portion 91 is displayed at the central portion of the screen of the monitor 4 with a marker 92 which is generated by the window pulse in order that the doctor can fix his eyes upon the morbid portion.

However, if the window marker 92 is always indicated on the screen of monitor 4, the observation might not be conducted well. Therefore, it is preferable that the doctor can selectively display the marker. To this end, a switch 93 for switching the indication of the window marker may be provided on the operating portion 14 of the video endoscope 2 as shown in FIG. 13.

FIG. 14 is a schematic view showing a major portion of the video endoscope of third embodiment of the video endoscope apparatus according to the present invention.

In this embodiment, an objective 97 fixed in a distal end portion 96 of a video endoscope 95 can be moved in the direction of the optical axis thereof by a wire 99 which is passed through an inserting portion 98.

One end of wire 99 is secured to a lens holder arranged slidably, and the other end of the wire 99 is connected to a rack gear 102 provided in the operating portion 101. This rack gear 102 is arranged so as to be moved by a pinion gear 104 which is coupled with a rotating shaft of a motor 103. And thus, the objective 97 can be moved in the direction of the optical axis thereof by means of the rotation of the motor 103 via the wire 99. Thus, even if the distance between the object and the objective is changed, a sharp image of the object is always formed on a CCD 105 by moving the objective 97. The wire 99 is biased to be pulled in one direction by a spring 106. In this embodiment, a driving signal is supplied to the motor 103 via a drive circuit, instead of the voltage amplifier for driving the piezoelectric element 26 of the first embodiment, and the automatic focusing control is conducted thereby. A reference numeral 107 represents the light guide for transmitting the illuminating light.

The function and effect of the third embodiment are almost same as those of the above mentioned first and second embodiments.

The present invention is not limited to the embodiments explained above, but many modifications may be conceived by those skilled in the art within the scope of the invention.

In the above embodiments, either one of the objective and image sensor is moved, but both of them may be moved. For instance, the vibration signal may be applied to the piezoelectric element of the first embodiment to vibrate the image sensor, and at the same time the focus error correction signal may be supplied to the moving coil of the second embodiment to displace the image sensor in the optical axis direction. This may be effected by passing the output signal of the mixing device 37 through high pass filter and low pass filter to derive the vibration signal and the focus error correction signal, respectively. In this case, after a predetermined period has been passed, the vibrating voltage applied to the piezoelectric element 26 may be cut off and the CCD may be positioned in the in-focused condition by means of the moving coil 82, or the vibrating voltage applied to the piezoelectric element 26 may be made smaller little by little so that the CCD 11 is fixed at the in-focused point. If the object is moving, it is preferable to vibrate the CCD all the time.

The automatic focus servo control circuit is provided in the signal processing device, but it may be arranged in the operating portion of the video endoscope.

FIG. 15 is a schematic view showing another embodiment of the displaying mode on the screen of the monitor 4. In the embodiment shown in FIG. 12, the image of the object to be observed is indicated on the monitor screen as a whole, but in this embodiment, on the left half of the screen, various kinds of data, for example, ID, initial, sex, birthday of patient, date of observation, etc. are displayed, and on the right half of the screen, the image of the object is displayed. In this case, since the area for displaying the image is rather small, it is not necessary to indicate the window marker. Therefore, the output signal of the video processor 25 may be directly supplied to the peak detector 41, that is to say, the analogue gate 58 and the window pulse generator 59 may be omitted from the apparatus shown in FIG. 4. In this case, the peak value on each full scanning line is detected.

As described above, according to the present invention, since the automatic focus control means is provided in the apparatus, the morbid portion can be observed with the aid of the sharp image, and it contributes to the precise and accurate judgment and diagnosis. Further, the focus condition of the object image on the image sensor is detected by vibrating them relative to each other in the direction of the optical axis of the objective and by synchronously detecting the peak value of the image signal supplied from the image sensor, it is no more necessary to arrange a separate light source for the focus detection and the whole apparatus can be made simple in construction, small in size and cheap in cost.

What is claimed is:

1. A video endoscope apparatus with an automatic focus control comprising
    a video endoscope including an insertion section to be insertable into an object under inspection and having a distal end and a proximal end, an objective lens system arranged within the distal end of the insertion section and forming an optical image of the object, and an image sensor arranged within the distal end of the insertion section and receiving the optical image of the object to produce an image signal;
    a signal processing unit connectable to said video endoscope and processing the image signal produced from said image sensor to derive a processed image signal;
    a monitor having a screen for displaying the processed image signal; and
    an automatic focus controlling means including an oscillator for producing a vibration signal, a vibrating means for vibrating said objective lens system and image sensor relative to each other in a direction of an optical axis of the objective lens system in accordance with the vibration signal supplied from the oscillator, a focus detecting means for detecting a focus condition of the optical image formed on the image sensor by the objective lens system by processing the image signal supplied from said image sensor, and a focus error correcting means for deriving a focus error correcting signal from the focus condition detected by said focus detecting means and moving said objective lens system and image sensor relative to each other in the direction of the optical axis of the objective lens system in accordance with said focus error correcting signal so as to attain the in-focused condition.

2. An apparatus according to claim 1, wherein said vibrating means and focus error correcting means comprise a common driving device for effecting the mutual movement between the objective lens system and image sensor in the direction of the optical axis of the objective lens system, and said vibration signal and focus error correcting signal are supplied to said common driving device in the superimposed manner.

3. An apparatus according to claim 2, wherein said common driving device comprises a piezoelectric element and said image sensor is secured to said piezoelectric element.

4. An apparatus according to claim 2, wherein said common driving device comprises a sliding member arranged slidably in the direction of the optical axis of the objective lens system, a moving coil secured to the sliding member, and a permanent magnet fixed to the distal end of the insertion section to be faced with said moving coil, and said image sensor is secured to the sliding member.

5. An apparatus according to claim 2, wherein said common driving device comprises a motor arranged within an operation section of the video endoscope, a pinion gear connected to the motor, a rack gear arranged slidably within the operation section and being engaged with said pinion gear, a wire extended within the insertion section and having one end connected to the rack gear and the other end connected to the objective lens system, and a spring arranged within the operation section and connected to the wire such that the wire is biased to be pulled in one direction.

6. An apparatus according to claim 1, wherein said focus detecting means comprises a peak detector for detecting a peak value of the image signal on respective scanning line, a band pass filter for passing a signal component of an output signal of the peak detector, a synchronous detector for synchronously detecting an output signal of the band pass filter with the aid of a sampling signal synchronized with said vibration signal, and a comparator for comparing an output signal of the synchronous detector with a predetermined reference value to derive the focus error correcting signal.

7. An apparatus according to claim 6, wherein said signal processing unit further comprises a window pulse generator for generating a window pulse by means of which a window having a given size may be displayed on the screen of the monitor.

8. An apparatus according to claim 7, wherein said focus detecting means comprises a gate for selectively supplying a portion of the image signal within the window.

9. An apparatus according to claim 8, wherein the frequencies of the vibration signal and the sampling signal are set to 10 Hz and a center frequency of the band pass filter is set to 10 Hz.

* * * * *